(12) United States Patent
Takeda

(10) Patent No.: US 8,889,237 B2
(45) Date of Patent: Nov. 18, 2014

(54) EXCIPIENT SYSTEM AND MEDICAL CONTAINER FOR ERYTHROCYTE ENRICHED LIQUID

(75) Inventor: Norihiko Takeda, Ashigarakami-gun (JP)

(73) Assignee: Terumo Kabushiki Kaisha, Shibuya, Tokyo (JP)

(*) Notice: Subject to any disclaimer, the term of this patent is extended or adjusted under 35 U.S.C. 154(b) by 0 days.

(21) Appl. No.: 13/580,641

(22) PCT Filed: Feb. 16, 2011

(86) PCT No.: PCT/JP2011/053209
§ 371 (c)(1),
(2), (4) Date: Aug. 22, 2012

(87) PCT Pub. No.: WO2011/105257
PCT Pub. Date: Sep. 1, 2011

(65) Prior Publication Data
US 2012/0321827 A1    Dec. 20, 2012

(30) Foreign Application Priority Data
Feb. 23, 2010  (JP) .................................. 2010-036932

(51) Int. Cl.
| B32B 1/00 | (2006.01) |
| A61K 9/14 | (2006.01) |
| A61K 31/265 | (2006.01) |
| C09K 15/06 | (2006.01) |
| A61M 1/02 | (2006.01) |
| A01N 1/02 | (2006.01) |
| A61J 1/10 | (2006.01) |

(52) U.S. Cl.
CPC .......... *A01N 1/0226* (2013.01); *A61M 1/0218* (2013.01); *A61M 1/0272* (2013.01); *A61J 1/10* (2013.01)
USPC ...... 428/34.1; 428/35.7; 428/36.92; 424/486; 252/407; 514/533

(58) Field of Classification Search
CPC .......... A01N 1/00; A01N 1/02; A01N 1/021; A01N 1/0226; A61M 1/0019; A61M 1/02; A61M 1/0272; A61J 1/05; A61J 1/10; B65D 1/00; B65D 33/00; B65D 37/00
USPC .......... 428/34.1, 34.8, 35.2, 35.5, 35.7, 36.9, 428/36.92; 424/400, 486; 435/2; 514/533; 252/407
See application file for complete search history.

(56) References Cited

U.S. PATENT DOCUMENTS

| 5,037,419 A | 8/1991 | Valentine et al. |
| 5,079,002 A | 1/1992 | Nagai et al. |
| 5,602,259 A * | 2/1997 | Boo et al. ...................... 549/313 |
| 7,220,538 B2 * | 5/2007 | Fischer et al. ................. 435/1.1 |

FOREIGN PATENT DOCUMENTS

| EP | 0 419 373 A1 | 3/1991 |
| EP | 0 537 863 A1 | 4/1993 |
| JP | 54-046810 A | 4/1979 |
| JP | 62-261962 A | 11/1987 |
| JP | 1-106824 A | 4/1989 |
| JP | 1-123147 A | 5/1989 |
| JP | 1-171562 A | 7/1989 |
| JP | 5-500319 A | 1/1993 |
| WO | 88/05302 A1 | 7/1988 |
| WO | 97/16967 A1 | 5/1997 |

OTHER PUBLICATIONS

Document entitled "Hlb Systems" from pharmcal.tripod.com web page, accessed Oct. 3, 2013.*
International Search Report (PCT/ISA/210) issued on Apr. 26, 2011, by the Japanese Patent Office as the International Searching Authority for International Application No. PCT/JP2011/053209.
Shigeru Sasakawa, "Future Red Cell Products", May 1992, vol. 161, No. 6, pp. 399-402 (with partial English language translation).
Jacques Saint-Blancard, "Properties of Red Blood Cell Concentrates Stored in PAGGS—Sorbitol", Annales Pharmaceutiques Francaises, 1995 (month unknown), vol. 53, No. 5, pp. 220-229.
Gyorgy et al., "Tocopherol and Hemolysis in Vivo and in Vitro" Annals of the New York Academy of Sciences, (Oct. 1, 1949), pp. 231-239, XP-055067821, Retrieved from the Internet: URL:http://onlinelibrary.wiley.com/ store/10.1111/j.1749-6632.1949.tb55274.x/asset/j.1749-6632.1949.tb55274.x.pdf?v=1&t=hi7expg5&s=684ce6d92a0a0057bbe52c3f115eeda54e858824 [retrieved on Jun. 21, 2013].
Sunagawa et al., "The Effect of Antioxidant against Oxidative Damage of Membrane Protein and Lipid in Red Blood Cell by Ultraviolet Radiation" Nippon lyo Masu Supekutoru Gakkai Koenshu, (Dec. 23, 1995), vol. 20, Coden: Nimken; Issn: 0916-085X, XP-002699272 (Abstract only 2 pages), retrieved from STN Database accession No. 1995:1000907.
Extended European Search Report issued on Jul. 24, 2013, by the European Patent Office in corresponding European Patent Application No. 11747221.7. (11 pages).

* cited by examiner

Primary Examiner — Walter B Aughenbaugh
(74) Attorney, Agent, or Firm — Buchanan, Ingersoll & Rooney PC

(57) ABSTRACT

Provided are an excipient system and a medical container for an erythrocyte enriched liquid. The excipient system is prepared by adding a hemolysis inhibitor and a surfactant to an erythrocyte storage solution. Herein, the surfactant has an HLB value of 13 or more, and the number of oxyethylene groups at a hydrophilic segment in the molecular structure of the surfactant is 20 or more. The inside of the medical container is filled with the excipient system for an erythrocyte enriched liquid.

8 Claims, 6 Drawing Sheets

EXCIPIENT SYSTEM AND MEDICAL CONTAINER FOR ERYTHROCYTE ENRICHED LIQUID

FIELD OF THE INVENTION

The present invention relates to an excipient system and a medical container used for preserving an erythrocyte enriched liquid for a long term.

BACKGROUND OF THE INVENTION

When whole blood or CRC (or concentrated red cell) or the like is preserved for a long term, so-called hemolysis is caused, thereby rupturing erythrocyte membranes to release hemoglobin into external surroundings. In the meantime, recently it has been demonstrated that di-2-ethylhexyl phthalate (DEHP), which has been widely applied as a plasticizer for a polyvinyl chloride resin constituting a medical container, has an effect able to prevent the hemolysis. Hence, whole blood or CRC, together with an erythrocyte storage solution are put to be mixed in a medical container made of a polyvinyl chloride resin plasticized by DEHP, so as to elute DEHP to be mixed with the whole blood or the CRC. This allows the hemolysis to be suppressed, improving the erythrocyte storage performance.

However, DEHP has other effects of rupturing platelets or the like, and the reproductive toxicity thereof is concerned. Those disadvantages make DEHP inappropriate to be used as an excipient for an erythrocyte enriched liquid in a viewpoint of physiological safety.

Hence, for the purpose of solving such disadvantages, Patent Documents 1 and 2 propose a process for containing vitamin E in a resin that composes a medical container for preserving (or storing) blood in order to prevent platelets from being lost by the rupturing thereof.

PRIOR ART DOCUMENTS

Patent Documents

[Patent Document 1] Japanese Unexamined Patent Application Publication No. H05-500319
[Patent Document 2] Japanese Examined Patent Application Publication No. H06-34820

DISCLOSURE OF THE INVENTION

Problems to be Solved by the Invention

However, the proposed methods in Patent Documents 1 and 2 may obtain a sufficient effect of suppressing the loss of platelets, while those methods only exert an insufficient effect on preserving erythrocytes. That is, vitamin E has a lower effect on the hemolysis inhibition than that of DEHP, resulting in poor performance on the erythrocyte storage.

Means for Solving the Problems

Accordingly, the present invention has been developed to solve the above mentioned disadvantages. Thus, an object of the present invention is to provide an excipient system and a medical container for an erythrocyte enriched liquid having a highly inhibitory effect on hemolysis and excellent in the erythrocyte storage performance.

Therefore, for the purpose of solving the above mentioned disadvantages, the excipient system for the erythrocyte enriched liquid of the present invention is prepared by adding a hemolysis inhibitor and a surfactant to an erythrocyte storage solution. Herein, an HLB (hydrophilic-lipophilic balance) value of the surfactant is 13 or more, and the number of oxyethylene groups at a hydrophilic segment in the molecule of the surfactant is 20 or more.

The above mentioned composition prepared by adding both hemolysis inhibitor and surfactant to the erythrocyte storage solution, allows the hemolysis inhibitory effect derived from the hemolysis inhibitor and the surfactant to be synergistically exerted. That is, the hemolysis inhibitor has an effect of covering an external surface of an erythrocyte membrane, thereby to inhibit the rupture of the erythrocyte membrane. Further, the surfactant promotes homogeneous dispersion of the hemolysis inhibitor molecules in the erythrocyte storage solution, thereby to cover the erythrocyte membranes with the hemolysis inhibitor. Moreover, the predetermined HLB value of the surfactant and the predetermined number of oxyethylene groups at the hydrophilic segment in the surfactant may inhibit the rupture of the erythrocyte membranes, even though the surfactant is applied alone.

Here, the excipient system for an erythrocyte enriched liquid of the present invention is composed of polyoxyethylene sorbitan at the hydrophilic segment in the molecular structure of the surfactant. Preferably, the erythrocyte storage solution is a mixed solution including mannitol, glucose, adenine, a phosphate salt, a citrate salt, and sodium chloride.

Further, the excipient system for an erythrocyte enriched liquid is composed of polyoxyethylene sorbitan at the hydrophilic segment in the molecular structure of the surfactant. Preferably, the erythrocyte storage solution is a mixed solution including mannitol, glucose, adenine, and sodium chloride.

Furthermore, the excipient system for an erythrocyte enriched liquid is composed of polyoxyethylene sorbitan at the hydrophilic segment in the molecular structure of the surfactant. Preferably, the erythrocyte storage solution is a mixed solution including sorbitol, glucose, adenine, guanosine, a phosphate salt, and sodium chloride.

Further, the excipient system for an erythrocyte enriched liquid is composed of polyoxyethylene at the hydrophilic segment in the molecular structure of the surfactant. Preferably, the erythrocyte storage solution is a mixed solution including mannitol, glucose, adenine, a phosphate salt, citric acid, and sodium chloride.

Further, the excipient system for an erythrocyte enriched liquid is composed of polyoxyethylene at the hydrophilic segment in the molecular structure of the surfactant. Preferably, the erythrocyte storage solution is a mixed solution including sorbitol, glucose, adenine, guanosine, a phosphate salt, and sodium chloride.

According to the above mentioned five types of compositions, the predetermined structure of the surfactant and the predetermined composition of the erythrocyte storage solution make the surfactant and the erythrocyte storage solution synergistically function, allowing the rupture of erythrocyte membranes to be further inhibited.

The excipient system for an erythrocyte enriched liquid of the present invention is characterized in that the hemolysis inhibitor is vitamin E. Further, the excipient system for an erythrocyte enriched liquid of the present invention is characterized in that the above mentioned vitamin E represents an acetate ester derivative.

According to the above mentioned composition, a feature that the hemolysis inhibitor is vitamin E, especially, an acetate ester derivative of vitamin E allows the rupture of erythrocyte membranes to be further inhibited due to an antioxidative effect of vitamin E and an affinitive interaction between an erythrocyte membrane and a lipid, or the like.

Further, the medical container of the present invention is characterized in that the aforementioned excipient system for an erythrocyte enriched liquid is filled inside the container itself.

According to the construction, the aforementioned excipient system for an erythrocyte enriched liquid is filled inside the container itself, allowing the rupture of the erythrocyte membranes of whole blood or CRC filled inside the container itself to be inhibited.

Advantageous Effects of the Invention

The excipient system for an erythrocyte enriched liquid and the medical container of the present invention may provide the equal or superior hemolysis inhibitory effect to the case that a conventional medical container composed of a polyvinyl chloride resin plasticized by DEHP is applied. Thus, the excipient system for an erythrocyte enriched liquid and the medical container of the present invention may have the excellent storage performance of erythrocytes.

EMBODIMENT FOR CARRYING OUT THE INVENTION

Next, embodiments of the excipient system for an erythrocyte enriched liquid of the present invention will be explained in detail.

The excipient system for an erythrocyte enriched liquid (hereinafter, referred to as the excipient system where necessary) is prepared by adding a hemolysis inhibitor and a surfactant to an erythrocyte storage solution. Herein, the surfactant has a predetermined molecular structure. The composition of the excipient system enables the rupture (or hemolysis) of erythrocyte membranes to be more inhibited than conventional DEHP (that is, a medical container composed of a polyvinyl chloride resin plasticized by DEHP). Note an addition amount of the excipient system is 40 mL to 60 mL per 100 mL of an erythrocyte enriched liquid, that is, 20 mL to 30 mL per 100 mL of collected blood. Then, each composition will be explained hereinafter.

(Hemolysis Inhibitor)

The hemolysis inhibitor prevents erythrocyte membranes from being ruptured by the antioxidation effect and the affinitive interaction between an erythrocyte membrane and a lipid or the like. More specifically, the hemolysis inhibitor preferably includes: vitamin E, or an unsaturated chain hydrocarbon compound selected from a group of 7-tetradecene, 8-octadecene, 9-eicosene, and squalene. Further, vitamin E includes: tocopherols such as α-tocopherol, β-tocopherol, γ-tocopherol and δ-tocopherol; and tocotrienols such as α-tocotrienol, β-tocotrienol, γ-tocotrienol and δ-tocotrienol or the like. Above all, α-tocopherol is most preferable. Moreover, vitamin E may include the ester derivatives of those tocopherols or tocotrienols, for example, an acetate ester derivative. More specifically, tocopherol acetate is most preferable.

Figure 5:
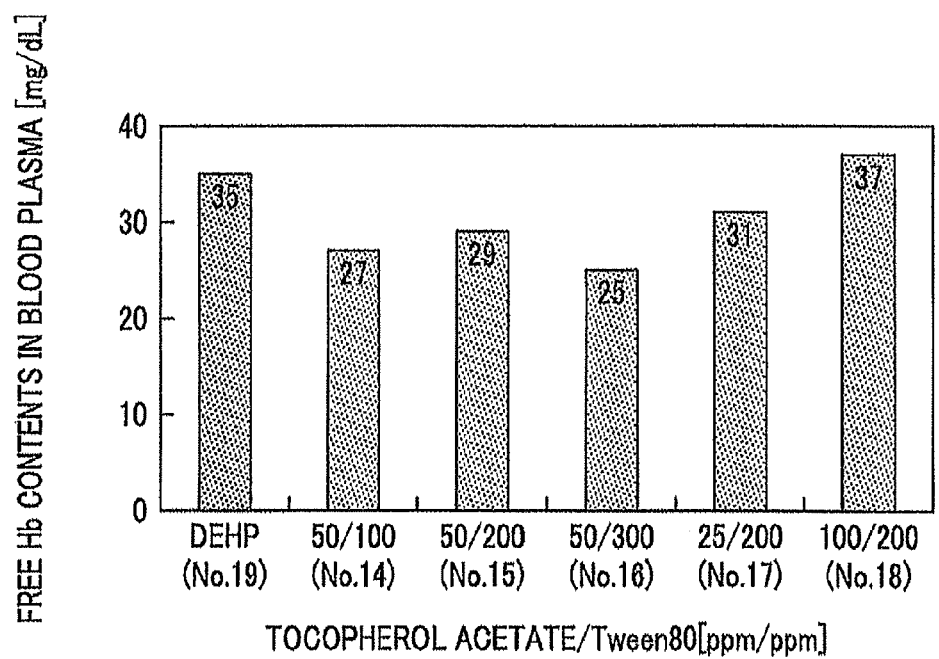
FIG. 5 is a graphic diagram showing the free Hb contents in the blood plasma through the mini bag tests when the concentration rate between the hemolysis inhibitor and the surfactant is changed.

The hemolysis inhibitor preferably has a concentration from 25 ppm to 100 ppm in an erythrocyte product (see FIG. 5). Hereby, when the hemolysis inhibitor and also the surfactant are added to the erythrocyte enriched liquid, the concentration of the hemolysis inhibitor in the excipient system is preferably 75 ppm to 300 ppm. If the concentration is less than 75 ppm, the rupture inhibition of erythrocyte membranes tends to be difficult. More specifically, the hemolysis inhibitory rate tends to decrease, in other words, the Hb content in blood plasma tends to increase. In contrast, if the concentration is more than 300 ppm, clear enhanced improvement is not observed for the inhibitory effect on the rupture of erythrocyte membranes, and likely to lead to the increase in cost.

(Surfactant)

The surfactant has effects of promoting homogeneous dispersion of the hemolysis inhibitor in the erythrocyte storage solution, and covering of erythrocyte membranes with the hemolysis inhibitor. Further, the surfactant alone may inhibit the rupture of erythrocyte membranes. For the above mentioned advantageous effects, the surfactant has an HBL value of 13 or more, preferably from 13 to 20, and the number of oxyethylene groups (or the EO number) at a hydrophilic segment in the molecular structure is 20 or more, more preferably, from 20 to 40. Moreover, the surfactant preferably has a first form composed of polyoxyethylene (POE) at the hydrophilic segment in the molecular structure, or a second form composed of polyoxyethylene sorbitan (POE sorbitan) at the hydrophilic segment in the molecular structure.

If the HLB value is less than 13, the surfactant molecules are not dispersed in the excipient system, resulting in failure of inhibiting the rupture of erythrocytes. Further, if the number of EO is less than 20, the molecular mass at the hydrophilic segment in the surfactant is low, resulting in failure of inhibiting the rupture of erythrocyte membranes. Moreover, if the HLB value is more than 20 or the EO number is more than 40, clear enhanced improvement is not observed on the rupture inhibition of erythrocyte membranes, and likely to lead to the increase in cost. Note the HLB value is measured by Griffin's method to be calculated by the following formula:

$$\text{HLB Value} = (20 \times \text{the total molecular mass at the hydrophilic segment})/(\text{molecular weight of the surfactant})$$

A surfactant in the first form includes, for example, polyoxyethylene oleyl ether (EMALGEN (registered trademark) 430), polyoxyethylene lauryl ether (EMALGEN (registered trademark) 130K) or the like (see Table 1).

A surfactant in the second form includes, for example, polyoxyethylene sorbitan monooleate (Tween (registered trademark) 80, polyoxyethylene sorbitan monostearate (Tween 60), polyoxyethylene sorbitan monolaurate (Tween 20) or the like (see Table 1).

Here, the surfactant preferably has a concentration from 100 ppm to 300 ppm in an erythrocyte product (see FIG. 5). Hence, when the surfactant and the hemolysis inhibitor are added together to an erythrocyte enriched liquid, the concentration of the surfactant in the excipient system is preferably from 300 ppm to 900 ppm. If the concentration thereof is less than 300 ppm, the rupture inhibition of erythrocyte membranes tends to be difficult. More specifically, the hemolysis inhibitory rate is likely to decrease, in other words, the Hb content in blood plasma is likely to increase. In contrast, if the concentration thereof is more than 900 ppm, the rupture inhibition of erythrocyte membranes tends to be difficult, and is likely to lead to the increase in cost.

(Erythrocyte Storage Solution)

As the erythrocyte storage solution, is used a conventionally known storage solution for preserving an erythrocyte enriched liquid for a long term. Such an erythrocyte storage solution includes: an ACD solution, a CPD solution, a MAP solution, a SAGM solution, OPTISOL (registered trademark) (or AS-5), ADSOL (or AS-1), Nutricel (or AS-3), PAGG-S, SAGP-maltose or the like. Among them, in particular, a MAP solution, a SAGM solution or PAGG-S is very preferable. Herein, the MAP solution is a mixed solution containing mannitol, glucose, adenine, a phosphate salt, citric acid and sodium chloride. Further, the SAGM solution is a mixed solution containing mannitol, glucose, adenine and sodium chloride. Moreover, PAGG-S is a mixed solution containing sorbitol, glucose, adenine, guanosine, a phosphate salt and sodium chloride.

Note the addition volume of the erythrocyte storage solution is 40 mL to 60 mL per 100 mL of the erythrocyte enriched liquid, that is, 20 mL to 30 mL per 100 mL of collected blood. If the addition amount thereof is less than the above mentioned minimum amount, the rupture inhibition of erythrocyte membranes tends to be difficult. In contrast, if the addition amount thereof is more than the above mentioned maximum amount, clear enhanced improvement of the rupture inhibition of erythrocyte membranes is not observed, and likely to lead to the increase in cost.

Next, a medical container of the present invention will be explained in detail.

Figure 6:
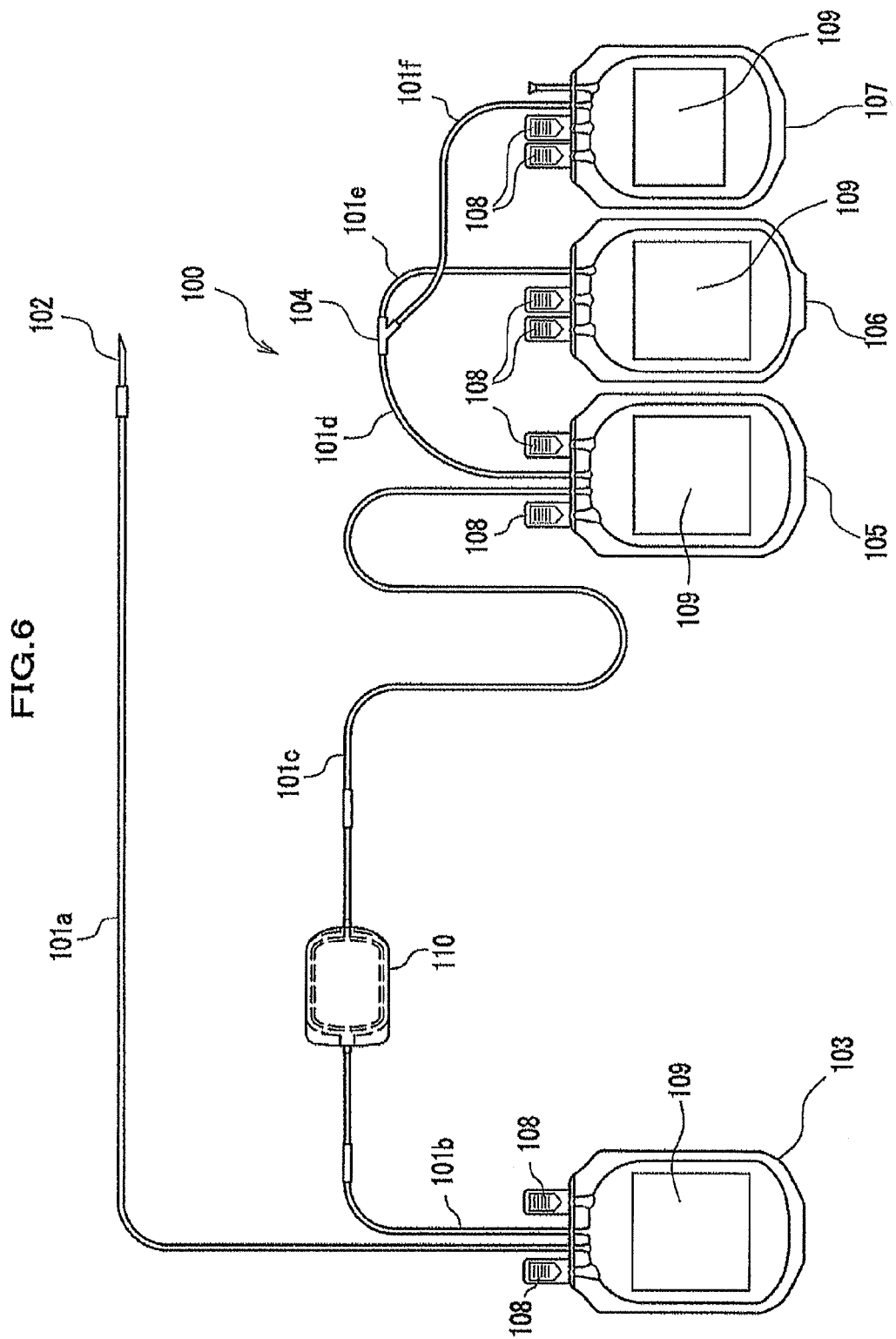
FIG. 6 is a schematic diagram showing a construction of the medical containers of the present invention.

The medical container is characterized in that the excipient system for an erythrocyte enriched liquid is filled inside the container itself. Further, the container itself is produced by fusing peripheries of two resin sheets made of polyolefine or a polyvinyl chloride resin or the like to adhere with each other, thereby forming a container shape. Moreover, the medical container of the present invention corresponds to a drug solution filling bag 107 in a blood bag system 100, as shown in FIG. 6.

The blood bag system 100 comprises: a blood collecting bag 103 filled with blood collected from a blood donor (or donor) via a blood collecting tube 101a having a blood collecting needle 102 at the end of the tube; a blood treatment filter 110 for separating predetermined blood components (or leukocytes and platelets) from the blood (or whole blood) transported via a tube 101b from the blood collecting bag 103; a blood storage hag 105 for collecting the blood from which the predetermined blood components have been removed by being passed through the blood treatment filter 110 and a tube 101c; a blood storage bag 106 to which the blood components (or blood plasma) centrifuged in the blood storage bag 105 are transported via a tube 101d, a branch pipe 104 and a tube 101e; and the drug solution filling bag 107 into which the above mentioned excipient system for a erythrocyte enriched liquid has been filled. The excipient system for a erythrocyte enriched liquid is transported to the blood storage bag 105 from the drug solution filling bag 107 via a tube 101f, the brunch pipe 104 and a tube 101d, thereby to be added to the blood components (or the erythrocyte enriched liquid) in the blood storage bag 105.

Note the blood collecting bag 103, the blood storage bags 105 and 106 and the drug solution filling bag 107 have, for example, a volume from about 100 mL to about 600 mL respectively.

Further, outlets 108 are formed at the upper periphery of each of the blood collecting bag 103, the blood storage bags 105 and 106, and the drug solution filling bag 107. Moreover, a label 109 for indicating the blood components filled in the target bag is pasted on each of the blood collecting bag 103, the blood storage bags 105 and 106, and the drug solution filling bag 107. Furthermore, a flow path sealing member not shown is arranged at any of the tubes 101b to 101f where necessary. Herein, the flow path sealing member is arranged at the state that a flow path inside a tube is blocked (or sealed), and opens the flow path by breaking the sealing.

EXAMPLES

Example 1

The following mini bag tests were conducted to evaluate each erythrocyte storage performance of the excipient system.

<Mini Bag Tests>

To each erythrocyte storage solution (100 mL of a MAP solution), one of the seven typed surfactants selected from the listed reagents in Table 1 (90 mg) and a hemolysis inhibitor (vitamin E: tocopherol acetate; 15 mg) were added together. Hereby, the excipient systems of Nos. 1-3 and 8-11 shown in Table 2 were prepared. Further, polyethylene glycol (MW=1000) was added instead of the surfactant, to prepare the excipient system No. 12 as shown in Table 2. Moreover, the excipient system of No. 13 shown in Table 2 was prepared by adding the hemolysis inhibitor (or vitamin E) alone without using any surfactant. Then, each excipient system (20 mL) and the erythrocyte enriched liquid (40 mL) were mixed to produce an erythrocyte product, which was preserved for five weeks kept at 4° C. in the mini bag made of a polyvinyl chloride (PVC) plasticized by tri(2-etylhexyl) trimellitate (TOTM). The concentration of the hemolysis inhibitor in the erythrocyte product was 50 ppm, and the concentration of the surfactant therein was 300 ppm at that time. Further, the erythrocyte product added with no surfactant was similarly preserved in the mini bag made of PVC resin plasticized by di-2-ethylhexyl phthalate (DEHP).

Figure 1:
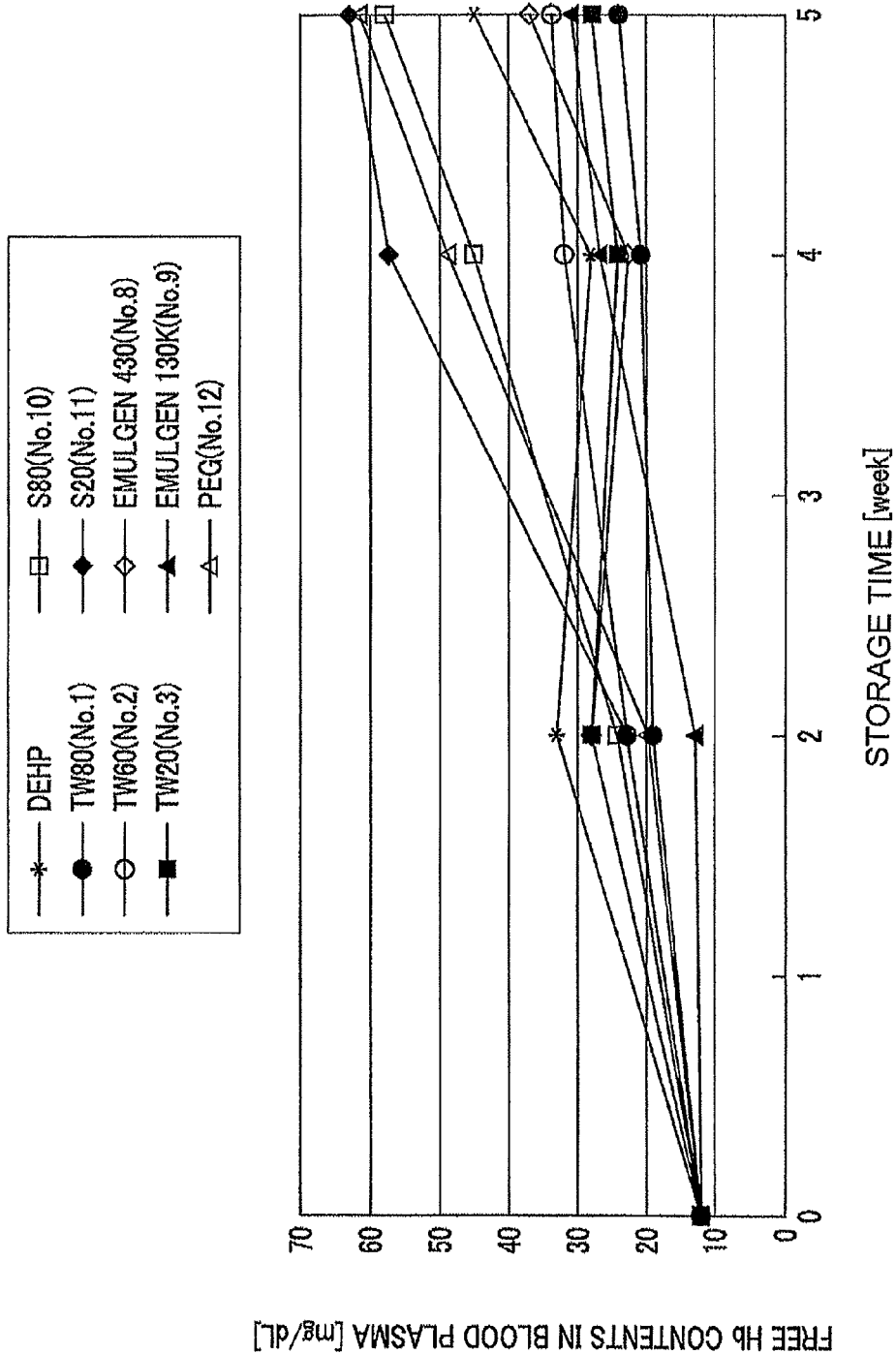
FIG. 1 is a graphic diagram showing changes in free Hb (or hemoglobin) contents in blood plasma through mini bag tests using various types of surfactants.
Figure 2:
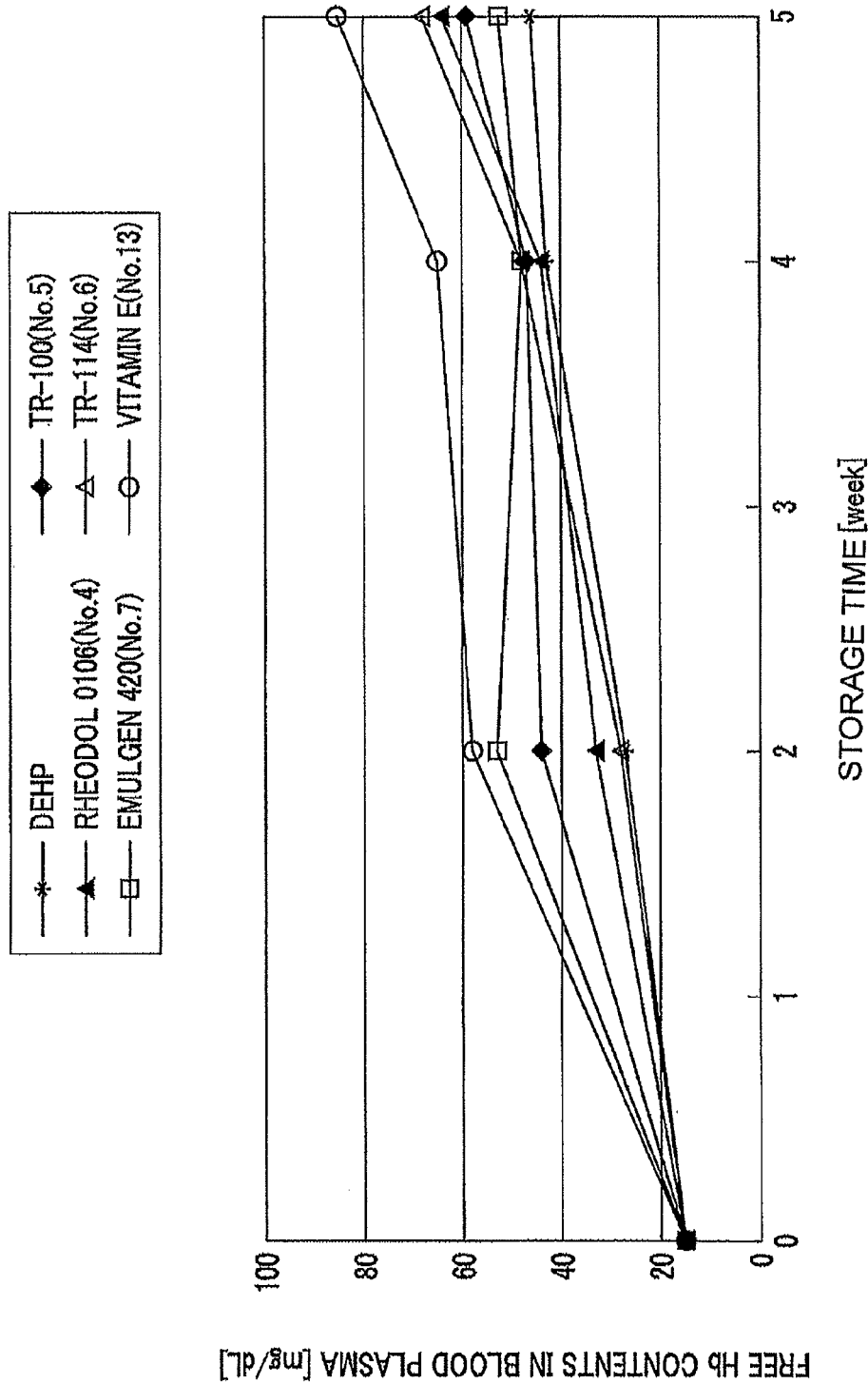
FIG. 2 is a graphic diagram showing the changes in the free Hb contents in the blood plasma through the mini bag tests using various types of the surfactants.

The free Hb contents in the blood plasma were measured using the following LCV method at the time points: before the preservation, after the two weeks preservation, after the four weeks preservation and after the five weeks preservation, of the erythrocyte product. Then, the erythrocyte storage performance was evaluated based on the following evaluation criteria. FIGS. 1 and 2 show the results.

(LCV Method)

The content of the free Hb (hemoglobin) in the blood plasma was measured in the following procedure.

(1) After Leuco Crystal Violet (20 mg) was dissolved in acetone (75 mL), acetic acid (20 mL) and RO (reverse osmosis) water (25 mL) were added to the prepared solution, thereby stirring and mixing the resultant solution. The obtained solution was used as a coloring reagent.

(2) To a hydrogen peroxide water (30 mass %, 1 mL), was added RO water (30 mL) to be mixed. The obtained solution was used as a coloring substrate solution.

(3) After the preservation of the erythrocyte product was completed, the erythrocyte product was centrifuged to collect a supernatant, which was used as a sample of measuring the free hemoglobin content in the blood plasma. Further, a standard hemoglobin solution (Alfresa Pharma Corporation, HEMOCON) was diluted with RO water, to simultaneously prepare standard hemoglobin solutions (that is, calibration curve samples) for creating a calibration curve by plotting 2 to 300 mg/dL of concentration points thereof.

(4) The coloring reagent (6 mL), the measuring sample and the calibration curve sample (25 μL) were added into a test tube and the mixture was stirred sufficiently.

(5) Further, to the above mixture, was added the coloring substrate solution (1 mL). The resultant mixture was stirred, and incubated in a water circulation typed incubator at 37° C. for 20 min.

(6) After the incubation was completed, the absorbance at 590 nm was measured by a spectrophotometer (U-3010, HITACHI LTD.). Then the hemoglobin concentration was calculated using a value of the calibration curve sample measured at the same time. The obtained value was used as the free hemoglobin content in the blood plasma.

(Evaluation Criteria of Erythrocyte Storage Performance)

If the free Hb content in the blood plasma of a test sample after preserving for five weeks in the mini bag was smaller than the free Hb content in the blood plasma derived from a reference sample which was preserved in the mini bag made of a PVC resin plasticized by DEHP, the erythrocyte storage performance was evaluated as "GOOD". In contrast, when the free Hb content in a test sample was larger than that of the reference sample, the erythrocyte storage performance was evaluated as "POOR".

Further, to the erythrocyte storage solutions (or MAP solutions, each 100 mL), were added four typed surfactants (each 60 mg) selected from the reagents listed in Table 1 and the hemolysis inhibitor (or vitamin E: tocopherol acetate, 15 mg) together, thereby preparing the excipient systems Nos. 4 to 7 shown in Table 2. Then, each excipient system (20 mL) and the erythrocyte enriched liquid (40 mL) were mixed to prepare an erythrocyte product. The resultant product was preserved for five weeks kept at 4° C. in the mini bag made of a polyvinyl chloride (PVC) resin plasticized by tri(2-ethylhexyl) trimellitate (TOTM). The concentration of the hemolysis inhibitor in the erythrocyte product was 50 ppm, and the concentration of the surfactant was 200 ppm at that time.

Further, the erythrocyte product added no excipient system was similarly preserved in the mini bag made of a PVC resin which was plasticized by di-2-ethylhexyl phthalate (DEHP). Accordingly, in the same method as mentioned hereinbefore, the free Hb content in the erythrocyte product was measured, so as to evaluate the erythrocyte storage performance thereof. The results were indicated in FIG. 2 and Table 2.

Example 2

The mini bag tests described below were conducted and each erythrocyte storage performance resulting from the excipient systems was evaluated.

<Mini Bag Tests>

To each erythrocyte storage solution (or a SAGM solution, 100 mL), were added respectively three typed surfactants (each 60 mg) selected from the surfactants listed in Table 1 together with a hemolysis inhibitor (or vitamin E: tocopherol acetate; 15 mg), thereby to prepare excipient systems Nos. 1, 4 and 9 shown in Table 2. Then, the respective excipient systems (each 20 mL) and the erythrocyte enriched liquid (40 mL) were mixed to produce an erythrocyte product, which was then preserved with kept at 4° C. for five weeks in the mini bag made of a PVC resin plasticized by tri(2-ethylhexyl) trimellitate (TOTM). Herein, the concentration of the hemolysis inhibitor was 50 ppm, and the concentration of the surfactant was 200 ppm in the erythrocyte product at that time. Further, the erythrocyte product added no excipient system was similarly preserved in the mini bag made of a PVC resin which was plasticized by di-2-ethylhexyl phthalate (DEHP).

Figure 3:
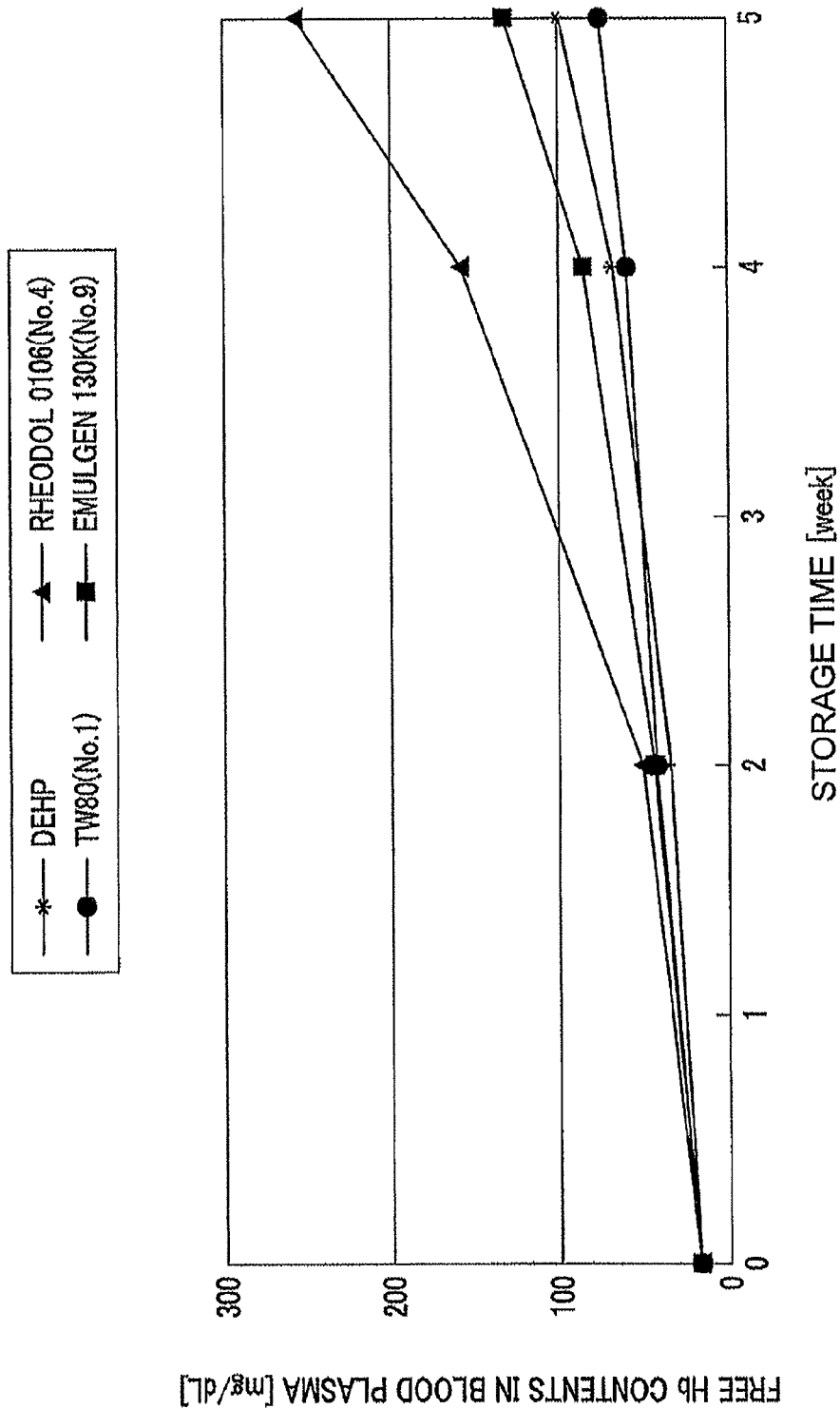
FIG. 3 is a graphic diagram showing the changes in the free Hb contents in the blood plasma through the mini bag tests using various types of the surfactants.

Accordingly, in the same method as in EXAMPLE 1, the free Hb content in the erythrocyte product was measured, so as to evaluate the erythrocyte storage performance thereof. The results were indicated in FIG. 3 and Table 2.

Example 3

The mini bag tests described below were conducted and each erythrocyte storage performance resulting from the excipient system was evaluated.

<Mini Bag Tests>

To respective erythrocyte storage solutions (or PAGG-S, each 100 mL), were respectively added three typed surfactants (each 60 mg) selected from the surfactants listed in Table 1 together with the hemolysis inhibitor (or vitamin E: tocopherol acetate, 15 mg), thereby to prepare excipient systems Nos. 1, 4 and 9 shown in Table 2. Then, each excipient system (20 mL) and the erythrocyte enriched liquid (40 mL) were mixed to produce an erythrocyte product, which was then preserved with kept at 4° C. for five weeks in the mini bag made of a PVC resin plasticized by tri(2-ethylhexyl) trimellitate (TOTM). Herein, the concentration of the hemolysis inhibitor was 50 ppm, and the concentration of the surfactant was 200 ppm in the erythrocyte product at that time.

Further, the erythrocyte product added no excipient system was similarly preserved in the mini bag made of a PVC resin which was plasticized by di-2-ethylhexyl phthalate (DEHP).

Figure 4:
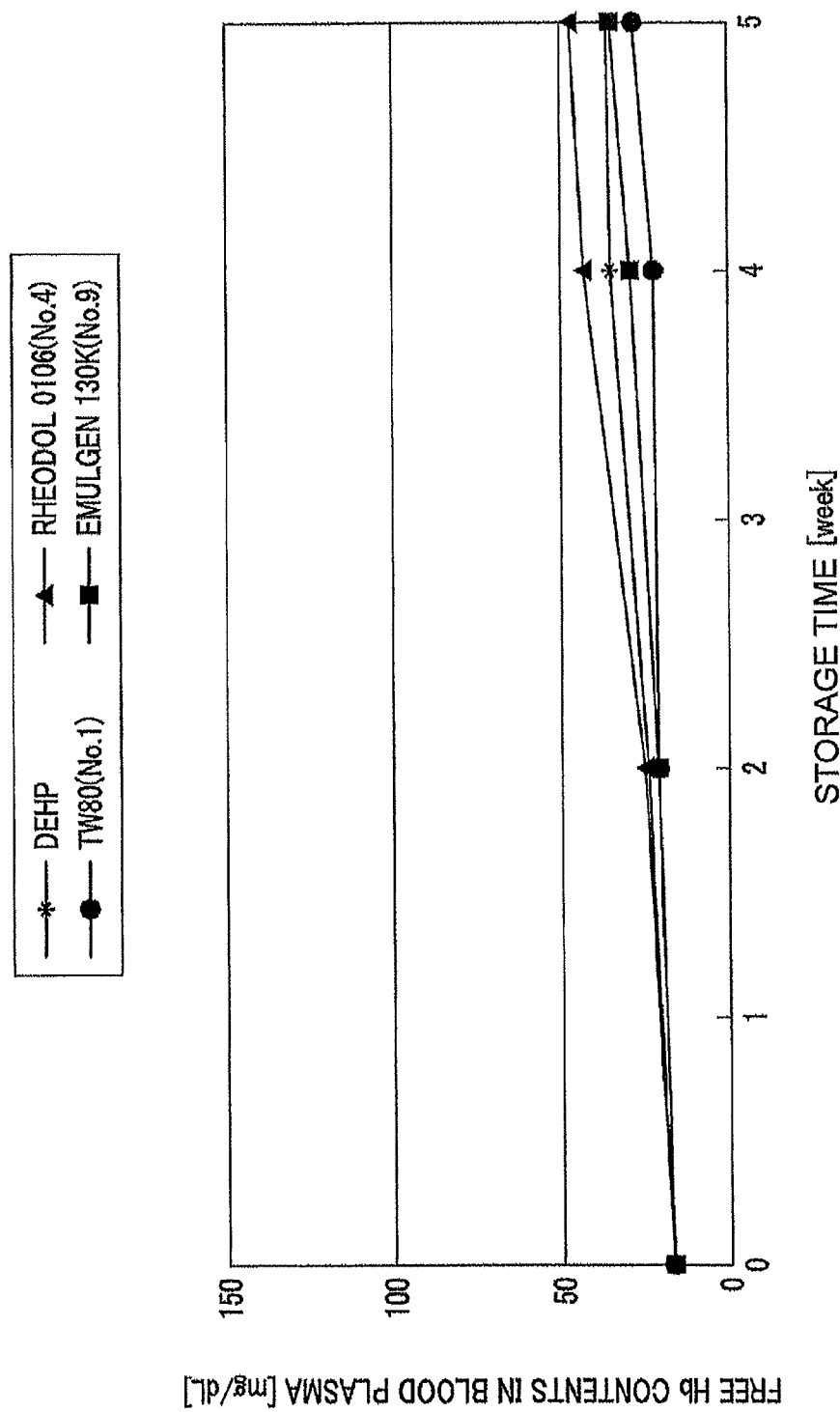
FIG. 4 is a graphic diagram showing the changes in the free Hb contents in the blood plasma through the mini bag tests using various types of the surfactants.

Accordingly, in the same method as in EXAMPLE 1, the free Hb content in blood plasma in the erythrocyte product was measured, so as to evaluate the erythrocyte storage performance thereof. The results were summarized in FIG. 4 and Table 2.

TABLE 1

| No. | Common Name | Abbriviation | Chemical Name of Compound | Hydrophobic Segment | Hydrophilic Segment | EO Number | HLB Value |
|---|---|---|---|---|---|---|---|
| 1 | Tween 80 | TW80 | Polyoxyethylene sorbitan monooleate | Aliphatic acid Ester | PEO Sorbitan | 20 | 15.0 |
| 2 | Tween 60 | TW60 | Polyoxyethylene sorbitan monostearate | | | 20 | 14.9 |
| 3 | Tween 20 | TW20 | Polyoxyethylene sorbitan monolaurate | | | 20 | 13.3 |
| 4 | Rheodol TW-O106 | RheoO106 | Polyoxyethylene sorbitan monooleate | | | 6 | 10.0 |
| 5 | Triton-X100 | TR-100 | Polyoxyethylene-p-t-octylphenyl ether | Alkyl Phenol | PEO | 10 | 13.5 |
| 6 | Triton-X114 | TR-114 | Polyoxyethylene-p-t-octylphenyl ether | | | 8 | 11.4 |
| 7 | Emulgen 420 | Emu420 | Polyoxyethylene oleyl ether | Aliphatic Ether | PEO | 13 | 13.6 |
| 8 | Emulgen 430 | Emu430 | Polyoxyethylene oleyl ether | | | 30 | 16.2 |

TABLE 1-continued

| No. | Common Name | Abbriviation | Chemical Name of Compound | Hydrophobic Segment | Hydrophilic Segment | EO Number | HLB Value |
|---|---|---|---|---|---|---|---|
| 9 | Emulgen 130K | Emu130K | Polyoxyethylene lauryl ether | | | 40 | 18.1 |
| 10 | Span 80 | S80 | Sorbitan Monooleate | Aliphatic acid Ester | Sorbitan | 0 | 4.3 |
| 11 | Span 20 | S20 | Sorbitan Monolaurate | | | 0 | 8.6 |

TABLE 2

| | No. | Hemolysis Inhibitor | Surfactant Abbreviation | Hydrophobic Segment | Hydrophilic Segment | EO Number | HLB Value | Erythrocyte Storage Performance (Mini Bag) Erythrocyte Storage Solution | | |
|---|---|---|---|---|---|---|---|---|---|---|
| | | | | | | | | MAP Solution | SAGM Solution | PAGG-S |
| EXAMPLE | 1 | Vitamin E | TW80 | Aliphatic acid Ester | PEO Sorbitan | 20 | 15.0 | GOOD | GOOD | GOOD |
| | 2 | | TW60 | | | 20 | 14.9 | GOOD | — | — |
| | 3 | | TW20 | | | 20 | 13.3 | GOOD | — | — |
| COMPARATIVE | 4 | | RHEOO106 | | | 6 | 10.0 | POOR | POOR | POOR |
| EXAMPLE | 5 | | TR-100 | Alkyl Phenol | PEO | 10 | 13.5 | POOR | — | — |
| | 6 | | TR-114 | | | 8 | 11.4 | POOR | — | — |
| | 7 | | EMU420 | Aliphatic Ether | PEO | 13 | 13.6 | POOR | — | — |
| EXAMPLE | 8 | | EMU430 | | | 30 | 16.2 | GOOD | — | — |
| | 9 | | EMU130K | | | 40 | 18.1 | GOOD | POOR | GOOD |
| COMPARATIVE | 10 | | S80 | Aliphatic acid Ester | Sorbitan | 0 | 4.3 | POOR | — | — |
| EXAMPLE | 11 | | S20 | | | 0 | 8.6 | POOR | — | — |
| REFERENCE | 12 | | PEG | — | — | 22 | — | POOR | — | — |
| EXAMPLE | 13 | Vitamin E Alone | | | | | | POOR | — | — |

(Note)
Vitamin E: Tocopherol Acetate

As shown in FIGS. 1 to 4 and Table 2, Examples 1 to 3, 8 and 9, which satisfied the requirements for the surfactant of the present invention, indicated "GOOD" erythrocyte storage performance. In contrast, COMPARATIVE EXAMPLES 4 to 7, 10 and 11, in which the rupture of erythrocyte membranes was not inhibited, indicated "POOR" erythrocyte storage performance. This was caused by at least either of the factors that the surfactant was not dispersed into the excipient system (or an aqueous solution) having the HLB value less than the lower limit in each COMPARATIVE EXAMPLE, and that the EO number less than the lower limit made the molecular mass at the hydrophilic segment in the surfactant so low. Further, REFERENCE EXAMPLES 1, 2 and 13 indicated "POOR" erythrocyte storage performance.

The above mentioned results demonstrated that the excipient systems used in EXAMPLES were superior to those used in COMPARATIVE EXAMPLES with respect to the erythrocyte storage performance. Further, the above mentioned results also demonstrated that the addition of the excipient systems shown in EXAMPLES had superior erythrocyte storage performance to the conventional medical container (eluting 30 ppm of the DEHP concentration) made by a polyvinyl chloride resin plasticized by DEHP; the medical container being used for preserving the erythrocyte product.

Example 4

To each erythrocyte storage solution (or a MAP solution, 100 mL), were added the respective amounts of a hemolysis inhibitor (or vitamin E: tocopherol acetate; 7.5 mg, 15 mg and 30 mg) and the respective amounts of a surfactant (or Tween 80; 30 mg, 60 mg and 90 mg) in various combination, thereby to prepare excipient systems Nos. 14 to 18 as listed in Table 3. Then, each excipient system (20 mL) and the erythrocyte enriched liquid (40 mL) were mixed to produce an erythrocyte product. Next, mini bag tests were conducted in the same method as in EXAMPLE 1, thereby to measure the free Hb contents in blood plasma. Herein, the concentrations of the hemolysis inhibitor and the surfactant in the erythrocyte product at that time are summarized in Table 3. Further, the same erythrocyte preservation test (No. 19), in which no hemolysis inhibitor and no surfactant were added, was conducted simultaneously using a mini bag made of a PVC resin plasticized by DEHP; the mini bag having the same compositional material as a conventional medical container.

As a result, if the free Hb content in blood plasma in the test sample was equal to or less than the free Hb content in the test No. 19, the erythrocyte storage performance in the mini bag test was evaluated as "GOOD." The results are summarized in FIG. 5 and Table 3.

TABLE 3

| | No. | Hemolysis Inhibitor (Vitamin E) Concentration (ppm) | Surfactant (Tween 80) Concentration (ppm) | Erythrocyte Storage Solution | Erythrocyte Storage Performance (Mini Bag) |
|---|---|---|---|---|---|
| EXAMPLE | 14 | 50 | 100 | MAP Solution | GOOD |
| | 15 | 50 | 200 | | GOOD |
| | 16 | 50 | 300 | | GOOD |

TABLE 3-continued

| No. | | Hemolysis Inhibitor (Vitamin E) Concentration (ppm) | Surfactant (Tween 80) Concentration (ppm) | Erythrocyte Storage Solution | Erythrocyte Storage Performance (Mini Bag) |
|---|---|---|---|---|---|
| | 17 | 25 | 200 | | GOOD |
| | 18 | 100 | 200 | | GOOD |
| REFERENCE EXAMPLE (DEHP) | 19 | 0 | 0 | | — |

(Note)
Vitamin E: Tocopherol Acetate

As shown in FIG. 5 and Table 3, it was confirmed that the excipient systems of the present invention had the equal or superior erythrocyte storage performance to the test sample (or REFERENCE EXAMPLE No. 19), in which the erythrocyte product was preserved in the conventional medical container (eluting 30 ppm of the DEHP concentration) composed of a polyvinyl chloride resin plasticized by DEHP.

Therefore, it should be noted that the above outstanding results were observed when the excipient systems of the present invention containing the hemolysis inhibitor (25 ppm to 100 ppm) and the surfactant (100 ppm to 300 ppm) were utilized and added (EXAMPLE Nos. 14-18).

DESCRIPTION OF REFERENCE NUMERALS

100 Blood Bag System
103 Blood Collecting Bag
105 Blood Storage Bag
106 Blood Storage Bag
107 Drug Solution Filling Bag (or Medical Container)
110 Blood Treatment Filter

The invention claimed is:

1. An excipient system suitable for being added to an erythrocyte enriched liquid, the excipient system comprising a hemolysis inhibitor and a surfactant, wherein
an HLB value of the surfactant is 13 or more; and
the number of oxyethylene groups at a hydrophilic segment in a molecular structure of the surfactant is 20 or more, and
wherein the hemolysis inhibitor is an acetate ester derivative of vitamin E present in a concentration in the excipient system of 75 ppm to 300 ppm.

2. A medical container, wherein the excipient system as described in claim 1 is filled inside the medical container itself.

3. The excipient system as described in claim 1, further comprising an erythrocyte storage solution.

4. The excipient system as described in claim 3, wherein
the hydrophilic segment in the molecular structure of the surfactant is composed of polyoxyethylene sorbitan;
the erythrocyte storage solution is a mixed solution containing mannitol, glucose, adenine, a phosphate salt, a citrate salt and sodium chloride.

5. The excipient system as described in claim 3, wherein
the hydrophilic segment in the molecular structure of the surfactant is composed of polyoxyethylene sorbitan;
the erythrocyte storage solution is a mixed solution containing mannitol, glucose, adenine and sodium chloride.

6. The excipient system as described in claim 3, wherein
the hydrophilic segment in the molecular structure of the surfactant is composed of polyoxyethylene sorbitan;
the erythrocyte storage solution is a mixed solution containing sorbitol, glucose, adenine, guanosine, a phosphate salt and sodium chloride.

7. The excipient system as described in claim 3, wherein
the hydrophilic segment in the molecular structure of the surfactant is composed of polyoxyethylene;
the erythrocyte storage solution is a mixed solution containing mannitol, glucose, adenine, a phosphate salt, a citrate salt and sodium chloride.

8. The excipient system as described in claim 3, wherein
the hydrophilic segment in the molecular structure of the surfactant is composed of polyoxyethylene;
the erythrocyte storage solution is a mixed solution containing sorbitol, glucose, adenine, guanosine, a phosphate salt and sodium chloride.

* * * * *